(12) United States Patent
Kamimoto et al.

(10) Patent No.: US 9,982,080 B2
(45) Date of Patent: May 29, 2018

(54) PHOTOCURABLE COMPOSITION AND HARD COATING AGENT

(71) Applicant: ADEKA CORPORATION, Tokyo (JP)

(72) Inventors: Tetsuo Kamimoto, Saitama (JP); Satoshi Masuda, Tokyo (JP); Fumihiko Sato, Saitama (JP); Yosuke Ishima, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 66 days.

(21) Appl. No.: 14/374,233

(22) PCT Filed: Mar. 5, 2013

(86) PCT No.: PCT/JP2013/055969
§ 371 (c)(1),
(2) Date: Jul. 24, 2014

(87) PCT Pub. No.: WO2013/146119
PCT Pub. Date: Oct. 3, 2013

(65) Prior Publication Data
US 2015/0005441 A1  Jan. 1, 2015

(30) Foreign Application Priority Data

Mar. 27, 2012  (JP) .................. 2012-070993

(51) Int. Cl.
*C08F 2/46* (2006.01)
*B32B 27/18* (2006.01)
(Continued)

(52) U.S. Cl.
CPC .......... *C08F 226/06* (2013.01); *C07D 251/24* (2013.01); *C08F 2/50* (2013.01);
(Continued)

(58) Field of Classification Search
CPC .. B32B 27/18; C08F 222/1006; C08F 226/06; C08F 290/00; C08F 2/50;
(Continued)

(56) References Cited

U.S. PATENT DOCUMENTS

2011/0195256 A1  8/2011  Morikawa et al.

FOREIGN PATENT DOCUMENTS

| JP | 11-071355 | | 3/1999 |
| JP | 1999-71355 | * | 3/1999 |

(Continued)

OTHER PUBLICATIONS

Machine translation for JP 2011-219623.*
(Continued)

*Primary Examiner* — Mark Eashoo
*Assistant Examiner* — Jessica M Roswell
(74) *Attorney, Agent, or Firm* — Young & Thompson

(57) ABSTRACT

A photocurable composition contains at least one ultraviolet absorber represented by Formula (1), and a hard coating agent including the photocurable composition.

(Continued)

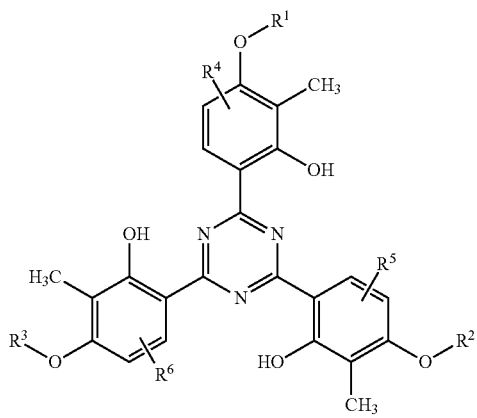

(1)

wherein $R^1$, $R^2$ and $R^3$ may be the same as or different from each other and represent a branched or linear alkyl group with 1-20 carbon atoms and is substituted with a (meth) acryloyloxy group; the alkyl group may be substituted with a hydroxyl group, an alkoxy group having 1-8 carbon atoms, or an acyloxy group having 1-8 carbon atoms; the alkyl group may be interrupted by an oxygen atom, a sulfur atom, a carbonyl group, an ester group, an amide group, or an imide group; and $R^4$, $R^5$ and $R^6$ may be the same as or different from each other and represent a hydrogen atom, a halogen atom, a hydroxyl group, an alkyl group having 1-12 carbon atoms, or an alkoxy group having 1-12 carbon atoms.

16 Claims, 1 Drawing Sheet

(51) Int. Cl.
| | |
|---|---|
| *C08F 290/00* | (2006.01) |
| *C09D 4/02* | (2006.01) |
| *C09D 7/12* | (2006.01) |
| *C09D 201/00* | (2006.01) |
| *C08F 226/06* | (2006.01) |
| *C08F 2/50* | (2006.01) |
| *C09D 5/32* | (2006.01) |
| *C09D 139/04* | (2006.01) |
| *C07D 251/24* | (2006.01) |
| *C08K 5/3492* | (2006.01) |
| *C08F 265/04* | (2006.01) |
| *C08F 290/06* | (2006.01) |
| *C09D 201/02* | (2006.01) |
| *C08F 222/10* | (2006.01) |
| *C08F 222/22* | (2006.01) |

(52) U.S. Cl.
CPC ........ *C08F 265/04* (2013.01); *C08F 290/067* (2013.01); *C08K 5/3492* (2013.01); *C09D 5/32* (2013.01); *C09D 7/48* (2018.01); *C09D 139/04* (2013.01); *C09D 201/02* (2013.01); *C08F 222/1006* (2013.01); *C08F 2222/225* (2013.01)

(58) Field of Classification Search
CPC .............. C08F 2222/225; C08F 265/04; C08F 290/067; C08F 222/225; C09D 139/04; C09D 201/00; C09D 5/32; C09D 7/1241; C07D 251/24; C08K 5/3492
USPC .......................................... 524/548; 526/261
See application file for complete search history.

(56) References Cited

FOREIGN PATENT DOCUMENTS

| | | | |
|---|---|---|---|
| JP | 11-181304 | | 7/1999 |
| JP | 2006-095929 | | 4/2006 |
| JP | 2007-230093 | | 9/2007 |
| JP | 2011-219623 | * | 4/2011 |
| JP | 2011-219623 | | 11/2011 |
| WO | 2010/024428 | | 3/2010 |

OTHER PUBLICATIONS

Machine translation for JP 1999-71355.*
International Search Report—PCT/JP2013/055969—dated Jun. 4, 2013.
Otsu, "Revised Chemical of High Molecular Synthesis," Japan, Kagaku-Dojin Publishing Company, Inc., The Second edition, Jan. 10, 1979.
Extended European Search Report—PCT/JP20131055969—dated Oct. 29, 2015.

* cited by examiner

PHOTOCURABLE COMPOSITION AND HARD COATING AGENT

TECHNICAL FIELD

The present invention relates to a photocurable composition containing an ultraviolet absorber. In addition, the invention relates to a hard coating agent comprising the photocurable composition.

BACKGROUND ART

Hitherto, as an input device of an information processing apparatus, a touch panel is known. The touch panel is equipped to the screen of an image display device and provides a predetermined instruction to an information processing apparatus by the position in the screen pressed. The outermost surface of the user's side of a large number of image display devices including an image display device mounted with a touch panel is provided with a hard coated film for scratch prevention.

In addition, opportunities to use an image display device outdoors have been increased along with the popularization of portable information devices such as a mobile phone or a notebook-sized personal computer, and a PDA (personal digital assistant). A hard coated film of the image display device for outdoor applications is required to have an excellent resistance to ultraviolet rays. It is needed the hard coated film does not turn yellow and the hard coating layer does not peel from the base film even exposed to ultraviolet rays for a long period of time.

A hard coated film has been formed on the surface not only of these touch panels or image display devices for outdoor applications, but also of a plastic molded product or a paint product such as a protective film or light shielding film for window glass of building or vehicle. These hard coated films have been formed in order to protect these surfaces and to provide excellent scratch resistance and stain resistance to these surfaces. However, these hard coated films themselves are degraded as exposed to ultraviolet rays for a long period of time, and thus peeling, cracking, or discoloration of the hard coated film gradually proceeds. In order to prevent such degradation, various means have been attempted. One of them is adding an ultraviolet absorber to the hard coated film so that durability to ultraviolet rays thereof can be improved.

It is preferable to use an organic resin composition as a material to form a hard coating layer since the hard coating layer can be easily formed by coating. Heating is required to cure the hard coating layer when a thermosetting resin is used as the resin. However, heating is undesirable since deformation of film or the like occurs by heating in a case in which the base material is a thin film. For this reason, a photocurable resin such as an ultraviolet curable resin to be cured by ultraviolet rays is generally used as a resin constituting the hard coating layer of hard coated film.

However, there is a problem that the hardness of coated film may be insufficient or the adhesion between the base film such as polyethylene terephthalate and the hard coated film may deteriorate by the influence of the ultraviolet absorber added in a case in which an ultraviolet curable resin is used as the resin constituting the hard coating layer.

Hence, Patent Literature 1 suggests a hard coated film, in which a hard coating layer containing an ultraviolet absorber, for example a benzotriazole-based compound, having a radically polymerizable (meth)acrylic functional group is formed on a base film. It is described that a large amount of ultraviolet absorber can be contained without imparting the hardness of the hard coating layer and thus a hard coating layer exhibiting high hardness and excellent ultraviolet absorption capacity can be realized in this case. However, the benzotriazole-based ultraviolet absorber does not exhibits satisfactory absorption wavelength or absorption capacity, and thus the effect thereof is insufficient.

Meanwhile, Patent Literature 2 suggests a triazine-based ultraviolet absorber having a (meth)acryloyl group. However, the use thereof to a photocurable composition is not described in this literature, and thus it is not possible to obtain the knowledge related thereto.

CITATION LIST

Patent Literature

Patent Literature 1: JP 2007-230093 A
Patent Literature 2: JP 11-71355 A

SUMMARY OF INVENTION

Technical Problem

Accordingly, an object of the invention is to provide a photocurable composition exhibiting excellent ultraviolet curability. In addition, another object of the invention is to provide a hard coating agent that comprises the photocurable composition and exhibits excellent hardness and adhesion to a base material.

Solution to Problem

The inventors has conducted intensive investigations in order to solve the problems described above, and as a result thereof, has found out a triazine-based ultraviolet absorber having a (meth)acryloyloxy group, thereby completing the invention.

The invention is to provide a photocurable composition containing one or more kinds of ultraviolet absorber represented by the following Formula (1).

[Chem. 1]

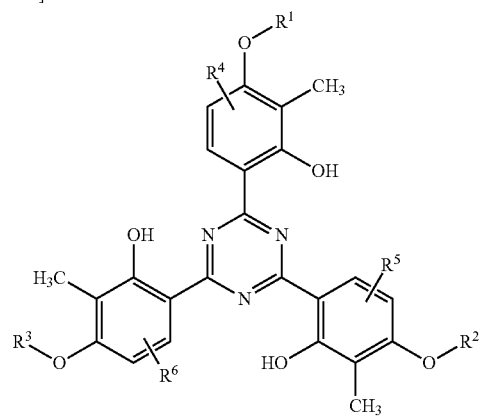

(1)

wherein $R^1$, $R^2$ and $R^3$ may be the same as or different from each other and represent a branched or linear alkyl group that has from 1 to 20 carbon atoms and is substituted with a (meth)acryloyloxy group; the alkyl group may be substituted with a hydroxyl group, an alkoxy group having from 1 to 8 carbon atoms, or an acyloxy group having from 1 to 8 carbon atoms; the alkyl group may be interrupted by one or more selected from an oxygen atom, a sulfur atom, a carbonyl group, an ester group, an amide group, and an imide group; and $R^4$, $R^5$ and $R^6$ may be the same as or different from each other and represent a hydrogen atom, a halogen atom, a hydroxyl group, an alkyl group having from 1 to 12 carbon atoms, or an alkoxy group having from 1 to 12 carbon atoms.

In addition, the invention is to provide a photocurable composition further containing one or more kinds selected from the group consisting of photocurable monomer, photocurable oligomer, and photocurable polymer, and one or more kinds of photopolymerization initiator.

Moreover, the invention is to provide the photocurable composition, in which the photocurable monomer, photocurable oligomer, and photocurable polymer have at least one (meth)acryloyl group.

Further, the invention is to provide a hard coating agent including the photocurable composition.

Furthermore, the invention is to provide a hard coated film obtained by forming a hard coating layer on a base film using the hard coating agent.

Effects of the Invention

According to the invention, it is possible to provide a photocurable composition exhibiting excellent ultraviolet curability. In addition, it is possible to provide an ultraviolet curable hard coating agent excellent in hardness and adhesion to a base material.

DESCRIPTION OF EMBODIMENTS

Figure 1:
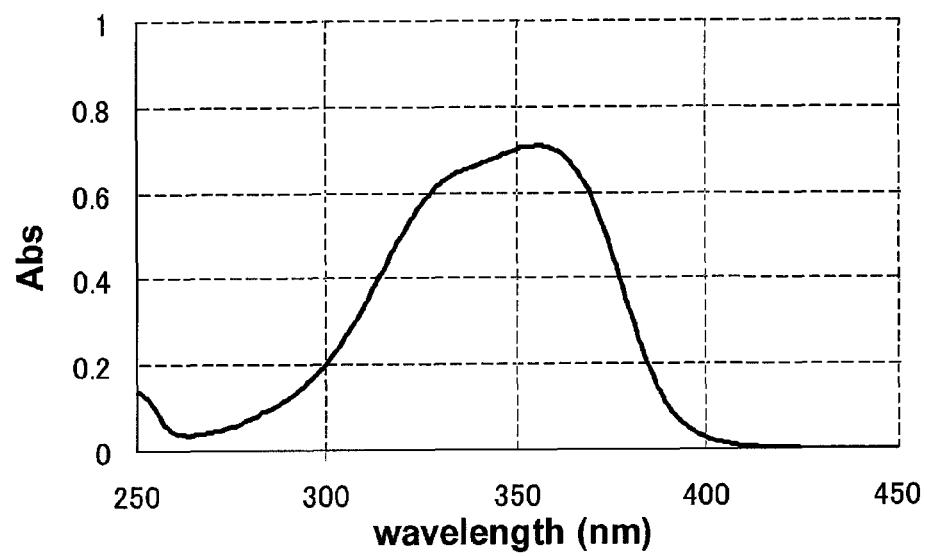
FIG. 1 is an absorption spectrum of Compound No. 2 obtained in Synthetic Example 1.

Hereinafter, the invention will be described in detail.

The photocurable composition of the invention contains one or more kinds of ultraviolet absorber represented by the following Formula (1):

[Chem. 2]

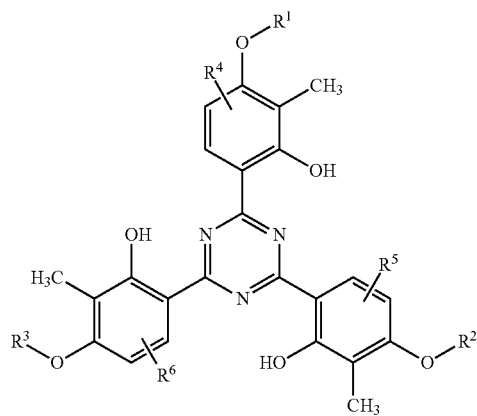

(1)

wherein $R^1$, $R^2$ and $R^3$ may be the same as or different from each other and represent a branched or linear alkyl group that has from 1 to 20 carbon atoms and is substituted with a (meth)acryloyloxy group; the alkyl group may be substituted with a hydroxyl group, an alkoxy group having from 1 to 8 carbon atoms, or an acyloxy group having from 1 to 8 carbon atoms; the alkyl group may be interrupted by one or more selected from an oxygen atom, a sulfur atom, a carbonyl group, an ester group, an amide group, and an imide group; and $R^4$, $R^5$ and $R^6$ may be the same as or different from each other and represent a hydrogen atom, a halogen atom, a hydroxyl group, an alkyl group having from 1 to 12 carbon atoms, or an alkoxy group having from 1 to 12 carbon atoms.

In Formula (1), the (meth)acryloyloxy group is a group represented by the following Formula (2), and the (meth)acryloyloxy group is an acryloyloxy group, in which $R^7$ in Formula (2) is a hydrogen atom or a methacryloyloxy group, in which $R^7$ in Formula (2) is a methyl group.

[Chem. 3]

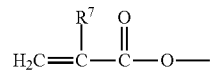

(2)

wherein $R^7$ represents a hydrogen atom or a methyl group.

In Formula (1), examples of the branched or linear alkyl group having from 1 to 20 carbon atoms include methyl, ethyl, n-propyl, isopropyl, n-butyl, isobutyl, sec-butyl, tert-butyl, n-pentyl, isopentyl, neopentyl, tert-amyl, 1,2-dimethylpropyl, n-hexyl, cyclohexyl, 1,3-dimethylbutyl, 1-isopropylpropyl, 1,2-dimethylbutyl, n-heptyl, 2-heptyl, 1,4-dimethylpentyl, tert-heptyl, 2-methyl-1-isopropylpropyl, 1-ethyl-3-methylbutyl, n-octyl, tert-octyl, 2-ethylhexyl, 2-methylhexyl, 2-propylhexyl, n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonadecyl, isononadecyl, n-icosyl, and isoicosyl. This alkyl group may be interrupted by one or more selected from an oxygen atom, a sulfur atom, a carbonyl group, an ester group, an amide group, and an imide group.

The position of substitution with the (meth)acryloyl group may be anywhere of the branched or linear alkyl group having from 1 to 20 carbon atoms.

In Formula (1), examples of the alkoxy group that has from 1 to 8 carbon atoms and may be substituted to the branched or linear alkyl group that has from 1 to 20 carbon atoms and is substituted with a (meth)acryloyloxy group, include an alkoxy group corresponding to an alkyl group having from 1 to 8 carbon atoms among the examples of the branched or linear alkyl group having from 1 to 20 carbon atoms.

In Formula (1), examples of the acyloxy group that has from 1 to 8 carbon atoms and may be substituted to the branched or linear alkyl group that has from 1 to 20 carbon atoms and is substituted with a (meth)acryloyloxy group, include an acyloxy group corresponding to an alkyl group having from 1 to 8 carbon atoms among the examples of the branched or linear alkyl group having from 1 to 20 carbon atoms.

In Formula (1), examples of the alkyl group that has from 1 to 12 carbon atoms and is represented by $R^4$, $R^5$ and $R^6$ include an alkyl group having from 1 to 12 carbon atoms among the examples of the branched or linear alkyl group having from 1 to 20 carbon atoms.

In Formula (1), examples of the alkoxy group that has from 1 to 12 carbon atoms and is represented by $R^4$, $R^5$ and $R^6$ include an alkoxy group corresponding to an alkyl group having from 1 to 12 carbon atoms among the examples of the branched or linear alkyl group having from 1 to 20 carbon atoms.

$R^1$, $R^2$ and $R^3$ are preferably an alkyl group that has from 1 to 8 carbon atoms and is substituted with a (meth)acryloyloxy group in terms of ultraviolet absorption capacity.

$R^4$, $R^5$ and $R^6$ are preferably a hydrogen atom in terms of ultraviolet absorption capacity.

Specific examples of the ultraviolet absorber that is represented by Formula (1) and used in the invention include the following Compounds Nos. 1 to 12, but are not limited to these compounds.

[Chem. 4]

Compound No. 1

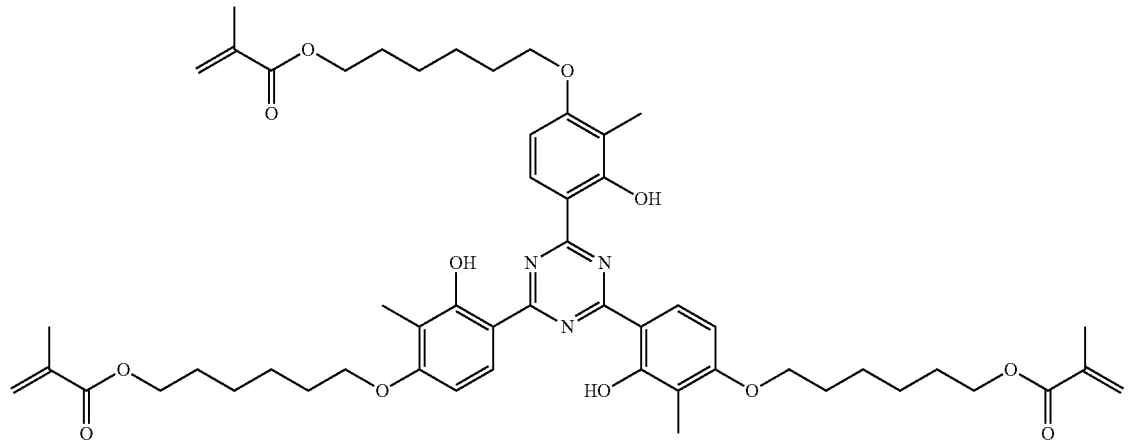

[Chem. 5]

Compound No. 2

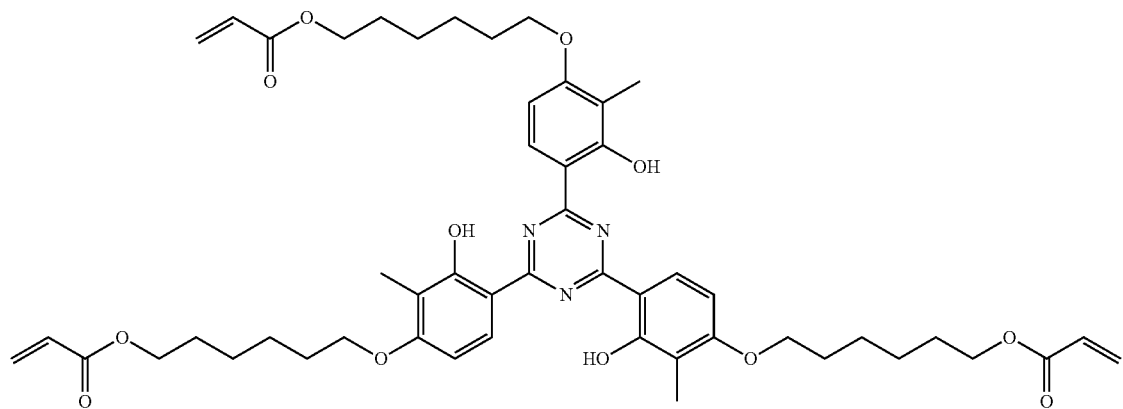

Compound No. 3

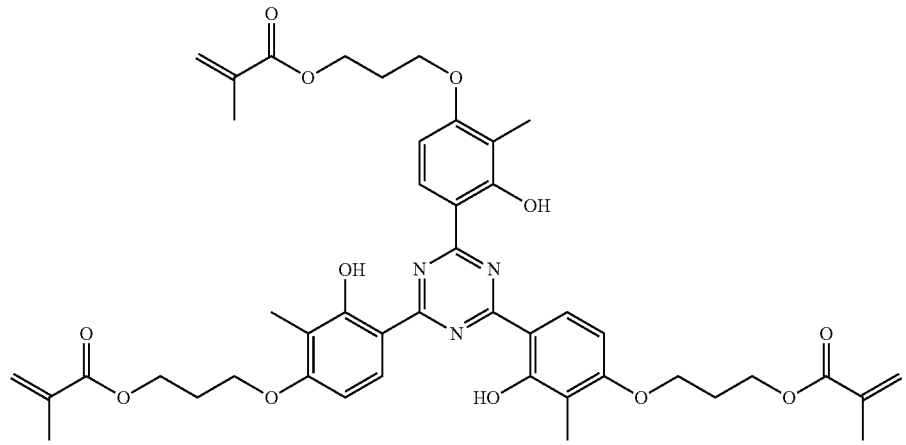

Compound No. 4
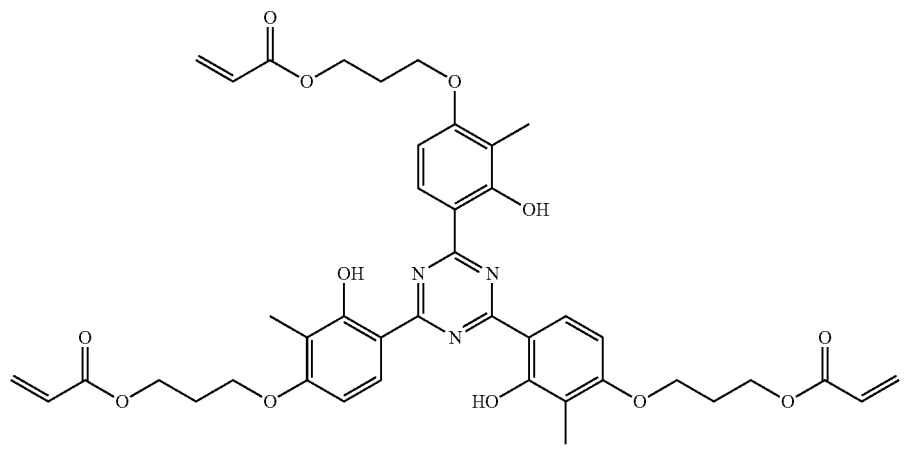
[Chem. 6]
Compound No. 5
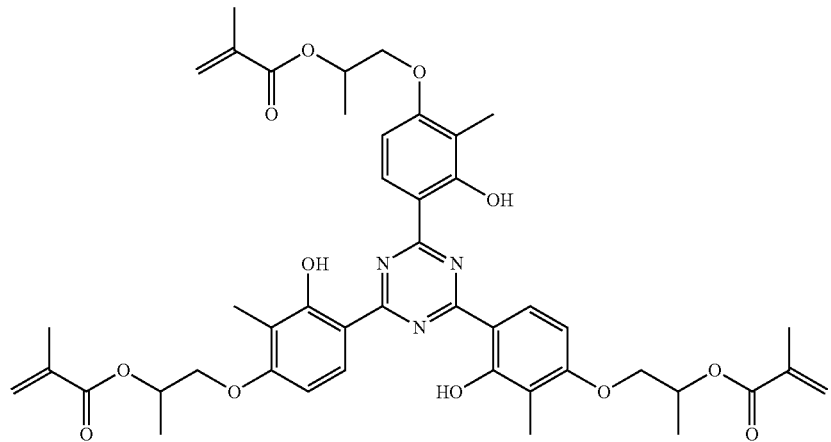
Compound No. 6
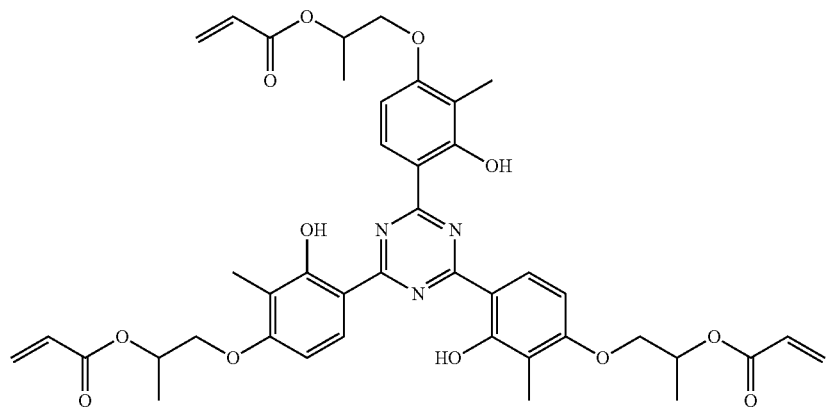

Compound No. 7
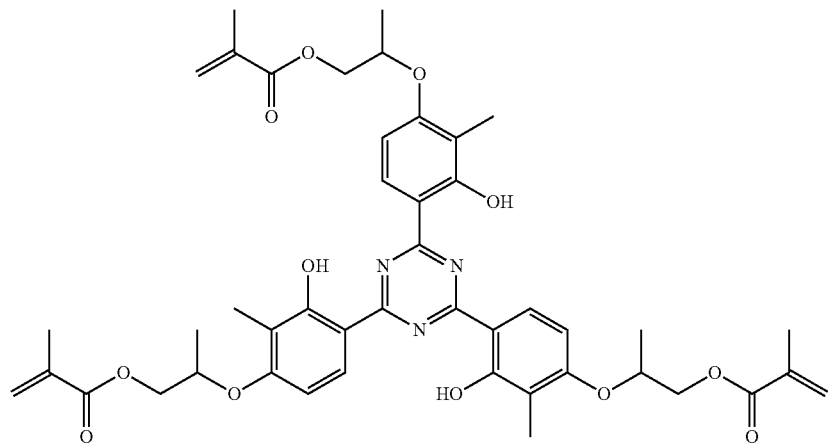
[Chem. 7]
Compound No. 8
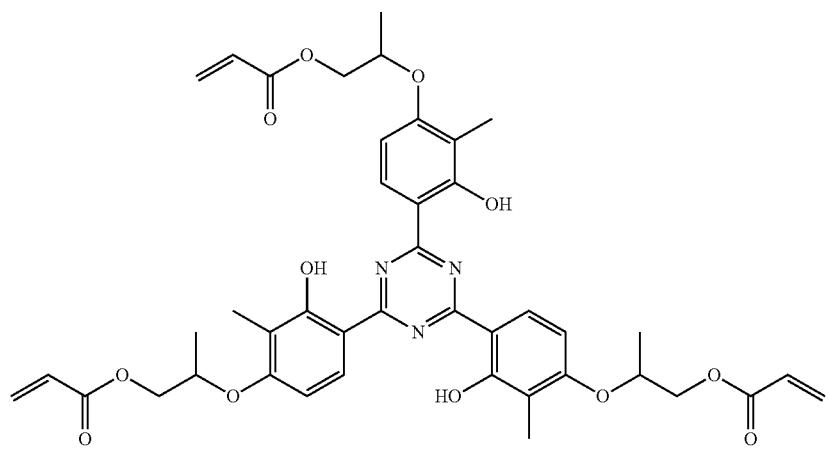
Compound No. 9
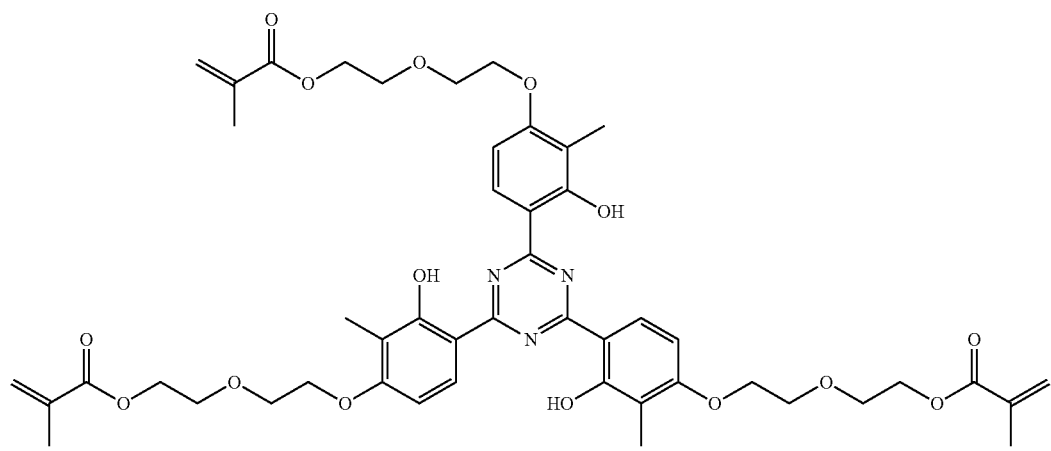

-continued

Compound No. 10

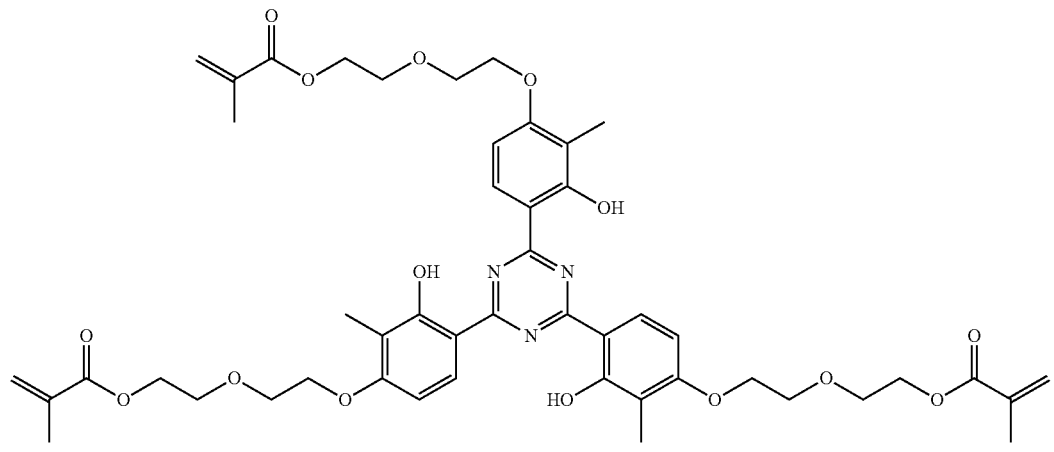

[Chem. 8]

Compound No. 11

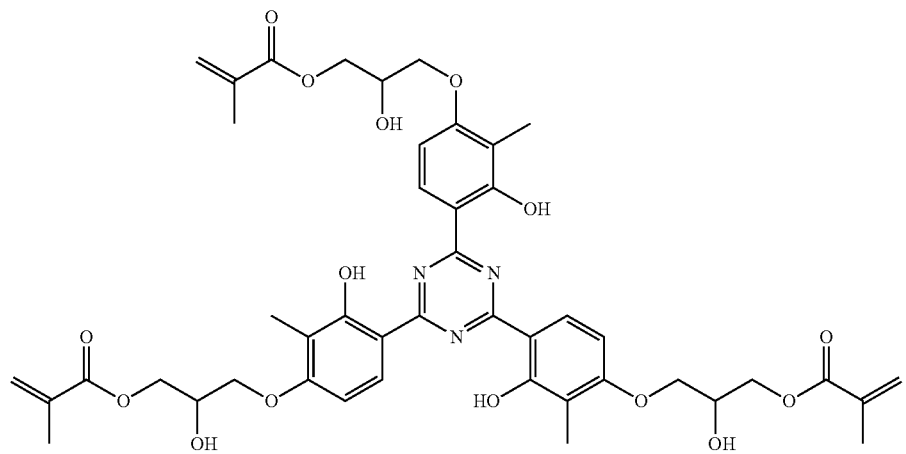

Compound No. 12

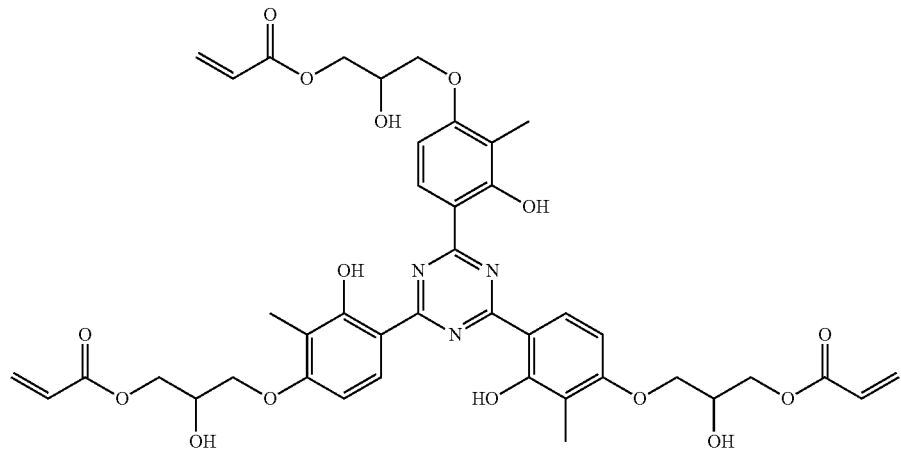

The content of the ultraviolet absorber of Formula (1) in the photocurable composition of the invention is preferably from 0.1 to 20.0% by mass and more preferably from 0.1 to 10.0% by mass of the solid components (components other than the solvent) in the photocurable composition.

There is a possibility that insufficient ultraviolet absorption capacity is obtained which may influence on the weather resistance of the cured product if the content of the ultraviolet absorber of Formula (1) is less than 0.1% by mass. There is a possibility that the physical properties of the cured product are adversely affected if the content thereof is more than 20.0% by mass.

Next, the synthetic method of the ultraviolet absorber represented by Formula (1) of the invention will be described.

The synthetic method of the ultraviolet absorber represented by Formula (1) is not particularly limited and may be any synthetic method used generally.

For example, Compound No. 1 is synthesized as follows. In a solvent, 3 moles of 2-methyl resorcinol is added to 1 mole of cyanuric chloride, thereby synthesizing 2,4,6-tris(2,4-dihydroxy-3-methylphenyl)triazine. This triazine is reacted with 3 moles of 6-chloro-1-hexanol and then the reaction product is reacted with methacrylic acid, thereby synthesizing 2,4,6-tris[2-hydroxy-3-methyl-4-(6-methacryloyloxy)hexyloxyphenyl]triazine (Compound No. 1).

The photocurable composition of the invention preferably contains one or more kinds selected from the group consisting of photocurable monomer, photocurable oligomer and photocurable polymer.

The photocurable monomer, photocurable oligomer and photocurable polymer are preferably a compound having one or more radically polymerizable functional group, and more preferably a (meth)acrylate compound having one or more (meth)acrylic functional group (for example, (meth) acryloyl group). The content of the photocurable monomer, photocurable oligomer, and photocurable polymer in the photocurable composition of the invention is preferably from 80 to 95% by mass of the solid components (components other than the solvent) in the photocurable composition.

Examples of the (meth)acrylate compound include ethyl (meth)acrylate, butyl(meth)acrylate, 2-ethylhexyl(meth) acrylate, nonyl(meth)acrylate, tridecyl(meth)acrylate, hexadecyl(meth)acrylate, octadecyl(meth)acrylate, isoamyl (meth)acrylate, isodecyl(meth)acrylate, isostearyl(meth) acrylate, cyclohexyl(meth)acrylate, benzyl(meth)acrylate, 2-hydroxyethyl(meth)acrylate, 3-chloro-2-hydroxypropyl (meth)acrylate, methoxyethyl(meth)acrylate, butoxyethyl (meth)acrylate, nonylphenoxyethyl(meth)acrylate, tetrahydrofurfuryl(meth)acrylate, glycidyl(meth)acrylate, 2-hydroxy-3-phenoxypropyl(meth)acrylate, nonylphenoxyethyl tetrahydrofurfuryl(meth)acrylate, caprolactone modified tetrahydrofurfuryl(meth)acrylate, diethylaminoethyl (meth)acrylate, an alkyldiol di(meth)acrylate such as 1,4-butanediol di(meth)acrylate, 3-methyl-1,5-pentanediol di(meth)acrylate, 1,6-hexanediol di(meth)acrylate, neopentyl glycol di(meth)acrylate, 2-methyl-1,8-octanediol di(meth)acrylate, and 2-butyl-2-ethyl-1,3-propanediol di(meth) acrylate, a polyoxy alkyl ether di(meth)acrylate such as ethylene glycol di(meth)acrylate, diethylene glycol di(meth) acrylate, dipropylene glycol di(meth)acrylate, tripropylene glycol di(meth)acrylate, and polypropylene glycol di(meth) acrylate, a di(meth)acrylate of diol having an alicyclic structure such as norbornane dimethanol diacrylate, norbornane diethanol di(meth)acrylate, a di(meth)acrylate of diol obtained by adding 2 moles of ethylene oxide or propylene oxide to norbornane dimethanol, 5-ethyl-5-hydroxymethyl-β,β-dimethyl-1-1,3-dioxan-2-ethanol diacrylate, tricyclodecane dimethanol di(meth)acrylate, tricyclodecane diethanol di(meth)acrylate, a di(meth)acrylate of diol obtained by adding 2 moles of ethylene oxide or propylene oxide to tricyclodecane dimethanol, pentacyclopentadecane dimethanol di(meth)acrylate, pentacyclopentadecane diethanol di(meth)acrylate, a di(meth)acrylate of diol obtained by adding 2 moles of ethylene oxide or propylene oxide to pentacyclopentadecane dimethanol, and a di(meth)acrylate of diol obtained by adding 2 moles of ethylene oxide or propylene oxide to pentacyclopentadecane diethanol, bis(2-acryloyloxyethyl)hydroxyethyl isocyanurate, bis(2-acryloyloxypropyl)hydroxypropyl isocyanurate, bis(2-acryloyloxybutyl)hydroxybutyl isocyanurate, bis(2-methacryloyloxyethyl)hydroxyethyl isocyanurate, bis(2-methacryloyloxypropyl)hydroxypropyl isocyanurate, bis(2-methacryloyloxybutyl)hydroxybutyl isocyanurate, trimethylolpropane tri(meth)acrylate, pentaerythritol tri (meth)acrylate, tris(2-acryloyloxyethyl) isocyanurate, tris(2-acryloyloxypropyl)isocyanurate, tris(2-acryloyloxybutyl) isocyanurate, tris(2-methacryloyloxyethyl)isocyanurate, tris (2-methacryloyloxy propyl) isocyanurate, tris(2-methacryloyloxybutyl)isocyanurate, poly(meth)acrylate of dipentaerythritol, an ethylene oxide modified phosphoric acid (meth)acrylate, an ethylene oxide modified alkylated phosphoric acid (meth)acrylate, a urethane (meth)acrylate, a multifunctional urethane (meth)acrylate, an epoxy(meth) acrylate, a urethane (meth)acrylate having a polyether backbone, a urethane (meth)acrylate having a polyester backbone, a polyester (meth)acrylate obtained by the esterification of a polyol of urethane (meth)acrylate having a polycarbonate backbone and (meth)acrylic acid, and a polyether (meth)acrylate obtained by the esterification of a polyol having a polyether backbone and (meth)acrylic acid.

The urethane (meth)acrylate is a compound having one acryloyl or methacryloyl group and one or more urethane bonds (—NHCOO—). The urethane (meth)acrylate is, for example, a reaction product of a polyol, a polyisocyanate, and a (meth)acrylate having a hydroxyl group. Here, examples of the polyol include ethylene glycol, 1,4-butanediol, neopentyl glycol, a polycaprolactone polyol, a polyester polyol, polycarbonate diol, and polytetramethylene glycol. Examples of the polyisocyanate include hexamethylene diisocyanate, isophorone diisocyanate, tolylene diisocyanate, xylylene diisocyanate, and 4,4'-diphenylmethane diisocyanate. Examples of the (meth)acrylate having a hydroxyl group include 2-hydroxyethyl(meth)acrylate, 2-hydroxypropyl(meth)acrylate, 1,4-butanediol mono(meth) acrylate, and ε-caprolactone adduct of 2-hydroxyethyl (meth)acrylate.

The multifunctional urethane (meth)acrylate is a compound having a plurality of acryloyl or methacryloyl group and one or more urethane bonds (—NHCOO—). The multifunctional urethane (meth)acrylate is, for example, a reaction product of a multifunctional (meth)acrylate having a hydroxyl group with a polyisocyanate. Examples of the multifunctional (meth)acrylate having a hydroxyl group include pentaerythritol tri(meth)acrylate, dipentaerythritol penta(meth)acrylate, and tripentaerythritol hepta(meth)acrylate. Examples of the polyisocyanate include tolylene diisocyanate, isophorone diisocyanate, xylylene diisocyanate, and hexamethylene diisocyanate.

The epoxy(meth)acrylate is, for example, a reaction product of a polyepoxy compound with (meth)acrylic acid. The polyepoxy compound is preferably a polyglycidyl compound. Specific examples thereof include a bisphenol A type epoxy resin, a bisphenol F type epoxy resin, a phenol novolak type epoxy resin, trisphenolmethane type epoxy resin, polyethylene glycol diglycidyl ether, glycerol polyglycidyl ether, and trimethylolpropane polyglycidyl ether.

N-vinyl pyrrolidone, N-vinyl caprolactam, a vinyl ether monomer, or the like can be used in addition to the (meth) acrylate compound as the radically polymerizable compound in the photocurable composition of the invention.

The photocurable composition of the invention preferably contains one or more kinds of photopolymerization initiator. The photopolymerization initiator has a function to generate a photoradical by being irradiated with ultraviolet rays and thus to initiate the polymerization of the photocurable monomer, photocurable oligomer, or photocurable polymer such as the (meth)acrylate compound described above.

As the photopolymerization initiator, for example, the following compounds can be included.

(1) Benzophenone derivatives: for example, benzophenone, methyl O-benzoylbenzoate, 4-benzoyl-4'-methyl diphenyl ketone, dibenzyl ketone, and fluorenone (2) Acetophenone derivatives: for example, 2,2'-diethoxyacetophenone, 2-hydroxy-2-methylpropiophenone, 2,2-dimethoxy-1,2-diphenyl-ethane-1-one (for example, IRGA-CURE 651 manufactured by BASF), 1-hydroxycyclohexyl phenyl ketone (for example, IRGACURE 184 manufactured by BASF, and Esacure KS300 manufactured by DKSH management Ltd./DKSH Holding Ltd.), 2-methyl-1-[4-(methylthio)phenyl]-2-morpholinopropan-1-one (for example, IRGACURE 907 manufactured by BASF), 2-hydroxy-1-{4-[4-(2-hydroxy-2-methylpropionyl)-benzyl]-phenyl}-2-methylpropan-1-one (for example, IRGACURE 127 manufactured by BASF), and methyl phenylglyoxylate (3) Thioxanthone derivatives: for example, thioxanthone, 2-methylthioxanthone, 2-isopropylthioxanthone, 4-isopropylthioxanthone, 2-chlorothioxanthone, and diethylthioxanthone (4) Benzyl derivatives: for example, benzyl, benzyl dimethyl ketal, and benzyl-β-methoxyethyl acetal (5) Benzoin derivatives: for example, benzoin, benzoin methyl ether, 2-hydroxy-2-methyl-1-phenylpropan-1-one (for example, DAROCURE 1173 manufactured by BASF)

(6) Oxime-based compounds: for example, 1-phenyl-1,2-butanedione-2-(O-methoxycarbonyl)oxime, 1-phenyl-1,2-propanedione-2-(O-methoxycarbonyl)oxime, 1-phenyl-1,2-propanedione-2-(O-ethoxycarbonyl)oxime, 1-phenyl-1,2-propanedione-2-(O-benzoyl)oxime, 1,3-diphenyl-propantrione-2-(O-ethoxycarbonyl)oxime, 1-phenyl-3-ethoxypropantrione-2-(O-benzoyl)oxime 1,2-octanedione, 1-[4-(phenylthio)-2-(O-benzoyloxime)]ethanone (for example, IRGACURE OXE01 manufactured by BASF), 1-[9-ethyl-6-(2-methylbenzoyl)-9H-carbazol-3-yl]-1-(O-acetyloxime) (for example, IRGACURE OXE02 manufactured by BASF)

(7) α-hydroxy ketone-based compounds: for example, 2-hydroxy-2-methyl-1-phenylpropan-1-one, 1-[4-(2-hydroxyethoxy)phenyl]-2-hydroxy-2-methyl-1-propan-1-one, and 2-hydroxy-1-{4-[4-(2-hydroxy-2-methylpropionyl)-benzyl]phenyl}-2-methylpropane (8) α-aminoalkylphenone-based compounds: for example, 2-benzyl-2-dimethylamino-1-(4-morpholinophenyl)-butanone-1 (for example, IRGACURE 369 manufactured by BASF), and 2-dimethylamino-2-(4-methylbenzyl)-1-(4-morpholin-4-yl-phenyl)butan-1-one (for example, IRGACURE 379 manufactured by BASF)

(9) Phosphine oxide-based compounds: for example, bis(2,4,6-trimethylbenzoyl)-phenylphosphine oxide (for example, IRGACURE 819 manufactured by BASF), bis(2,6-dimethoxyphenyl)-2,4,4-trimethyl-pentylphosphine oxide, and 2,4,6-trimethylbenzoyl-diphenyl-phosphine oxide (for example, DAROCURE TPO manufactured by BASF)

(10) Titanocene compounds: for example, bis(η5-2,4-cyclopentadien-1-yl)-bis(2,6-difluoro-3-(1H-pyrrol-1-yl)phenyl)titanium (IRGACURE 784 manufactured by Ciba Japan K.K.)

The content of the photopolymerization initiator is preferably from 0.1 to 10% by mass, more preferably from 0.1 to 5% by mass, and most preferably from 0.1 to 1% by mass in the solid components (components other than the solvent) of the photocurable composition. There is a possibility that the curing is insufficient if the content thereof is less than 0.1% by mass, and there is a possibility that the physical properties of the cured product are adversely affected if the content thereof is more than 10% by mass.

A curing accelerator (sensitizer) can be concurrently used together with the photopolymerization initiator in the photocurable composition of the invention. Examples of the concurrently usable curing accelerator (sensitizer) include an amine such as triethanolamine, diethanolamine, N-methyldiethanolamine, 2-methylaminoethyl benzoate, dimethylaminoacetophenone, p-dimethylaminobenzoic acid isoamyl ester, and p-dimethylaminobenzoic acid ethyl ester, and a hydrogen donor such as 2-mercaptobenzothiazole. Examples of a dye sensitizer include xanthene, thioxanthene, coumarin, and thiocoumarin.

An ultraviolet absorber other than Formula (1) may be blended in the photocurable composition of the invention in a range that the effect of the invention is not impaired.

Examples of the ultraviolet absorber include 2-hydroxybenzophenones such as 2,4-dihydroxybenzophenone, 2-hydroxy-4-methoxybenzophenone, 2-hydroxy-4-octoxybenzophenone, 5,5'-methylenebis(2-hydroxy-4-methoxybenzophenone); 2-(2'-hydroxyphenyl)benzotriazoles such as 242'-hydroxy-5'-methylphenyl)benzotriazole, 2-(2'-hydroxy-3',5'-di-tert-butylphenyl)-5-chlorobenzotriazole, 2-(2'-hydroxy-3'-tert-butyl-5'-methylphenyl)-5-chlorobenzothiazole, 2-(2'-hydroxy-5'-tert-octylphenyl)benzotriazole, 2-(2'-hydroxy-3',5'-dicumylphenyl)benzotriazole, 2,2'-methylenebis(4-tert-octyl-6-(benzotriazolyl)phenol), and 2-(2'-hydroxy-3'-tert-butyl-5'-carboxyphenyl)benzotriazole; benzoates such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate, and hexadecyl-3,5-di-tert-butyl-4-hydroxybenzoate; substituted oxanilides such as 2-ethyl-2'-ethoxyoxanilide and 2-ethoxy-4'-dodecyloxanilide; a cyanoacrylate such as ethyl-α-cyano-β,β-diphenyl acrylate and methyl-2-cyano-3-methyl-3-(p-methoxyphenyl)acrylate; and a triaryl triazine such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine, and 2-(2-hydroxy-4-propoxy-5-methylphenyl)-4,6-bis(2,4-di-tert-butylphenyl)-s-triazine.

A hindered amine-based light stabilizer may be blended in the photocurable composition of the invention in a range that the effect of the invention is not impaired.

Examples of the hindered amine-based light stabilizer include a hindered amine compound such as 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl) sebacate, bis(1,2,2,6,6-tetramethyl-4-piperidyl) sebacate, bis(1-octoxy-2,2,6,6-tetramethyl-4-piperidyl)sebacate, tetrakis(2,2,6,6-tetramethyl-4-piperidyl)-1,2,3,4-butane tetracarboxylate, tetrakis(1,2,2,6,6-pentamethyl-4-piperidyl)-1,2,3,4-butane tetracarboxylate, bis(2,2,6,6-tetramethyl-4-piperidyl)-di(tridecyl)-1,2,3,4-butane tetracarboxylate, bis(1,2,2,6,6-pentamethyl-4-piperidyl)-di(tridecyl)-1,2,3,4-butane tetracarboxylate, bis(1,2,2,4,4-pentamethyl-4-piperidyl)-2-butyl-2-(3,5-di-tert-butyl-4-hydroxybenzyl) malonate, a polycondensate of 1-(2-hydroxyethyl)-2,2,6,6-tetramethyl-4-piperidinol/diethyl succinate, a polycondensate of 1,6-bis(2,2,6,6-tetramethyl-4-piperidylamino)hexane/2,4-dichloro-6-morpholino-s-triazine, a polycondensate of 1,6-bis(2,2,6,6-tetramethyl-4-piperidylamino)hexane/2,4-dichloro-6-tert-octylamino-s-triazine, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazine-6-yl]-1,5,8-12-tetraazadodecane, 1,6,11-tris[2,4-bis(N-butyl-N-(2,2,6,6-tetramethyl-4-piperidyl)amino)-s-triazine-6-yl]aminoundecane, and 1,6,11-tris[2,4-bis(N-butyl-N-(1,2,2,6,6-pentamethyl-4-piperidyl)amino)-s-triazine-6-yl]aminoundecane.

A solid particulate may be blended in the photocurable composition of the invention in order to impart antiglare property to the cured film (for example, a hard coated film coated on a synthetic resin film).

As the solid particulate, an inorganic particulate and an organic particulate are exemplified.

As the inorganic particulate, an inorganic particulate having a volume average particle size of from 0.01 to 5 µm, for example carbon black, silica (fine powder of silicic acid, hydrated silicic acid, diatomaceous earth, colloidal silica, or the like), a salt of silicic acid (talc or the like), a salt of carbonic acid (precipitated calcium carbonate, magnesium carbonate, or the like), clay, alumina (a hydrate), barium sulfate (barite powder, precipitated barium sulfate, lithopone, or the like), gypsum, white lead, mica, zinc white, titanium oxide, and a microballoon (shirasu, glass, or the like) may be included, and two or more kinds of these inorganic particulates may be concurrently used.

The shape of the inorganic particulate may be any shape such as a spherical shape, a needle shape, a petal-like shape, or an irregular shape. The inside of the particulate may be any shape such as a hollow shape or a porous shape. The inorganic particulate may be obtained by a dry granulation or a wet granulation.

As the organic particulate, an azo pigment, a polycyclic pigment, and an organic resin bead (an acrylic bead, a polystyrene bead, a urethane bead, an epoxy bead or the like having a volume average particle size of from 0.1 to 2 µM by the Coulter counter method) are exemplified. Two or more kinds of these organic particulates may be concurrently used.

The shape of the organic particulate may be any shape such as a spherical shape, a needle shape, a petal-like shape, or an irregular shape. The inside of the particulate may be any shape such as a hollow shape or a porous shape. The organic particulate may be obtained by a dry granulation or a wet granulation.

The shape of the solid particulate preferably has a hollow or porous inside, and also preferably has a spherical shape from the view point of antiglare property of the cured film.

A dispersant may be blended in a case in which a solid particulate is blended. As the dispersant, a high molecular weight organic dispersant, a low molecular weight organic dispersant, and an inorganic dispersant are exemplified.

Examples of the high molecular weight organic dispersant include formalin condensate of naphthalene sulfonic acid salt, a salt of polystyrene sulfonic acid, a salt of polyacrylic acid, carboxymethyl cellulose, a salt of polycarboxylic acid, and polyvinyl alcohol.

Examples of the low molecular weight organic dispersant include a polyoxyalkylene diol type dispersant, a polyhydric alcohol type dispersant, a carboxylic acid salt type dispersant, a sulfuric acid ester type dispersant, a sulfonic acid salt dispersant, a phosphoric acid ester type dispersant, a primary to tertiary amine salt type dispersant, and a quaternary ammonium salt type dispersant.

Examples of the inorganic dispersant include a phosphoric acid compound such as a polyphosphoric acid salt and phosphoric acid.

An antifoaming agent may be blended in the photocurable composition of the invention.

Examples of the antifoaming agent include a lower alcohol (having from 1 to 4 carbon atoms, for example, methanol and butanol), a higher alcohol (having from 6 to 30 carbon atoms, for example, octyl alcohol and hexadecyl alcohol), a fatty acid (having from 4 to 30 carbon atoms, for example, oleic acid and stearic acid), a fatty acid ester (having from 7 to 36 carbon atoms, for example, glycerin monolaurate), a phosphoric acid ester (having from 6 to 20 carbon atoms, for example, tributyl phosphate), a metal soap (having from 18 to 30 carbon atoms, for example calcium stearate and aluminum stearate), a mineral oil, a polyether (for example PEG and PPG), and silicone (for example, dimethyl silicone oil, alkyl modified silicone oil, and fluorosilicone oil).

A silane coupling agent may be blended in the photocurable composition of the invention.

Examples of the silane coupling agent include an amine-based compound (γ-aminopropyltriethoxysilane, γ-aminopropyltrimethoxysilane, γ-phenylaminopropyltrimethoxysilane, or the like), a ureido-based compound (ureidopropyltriethoxysilane, or the like), a vinyl compound (vinyl ethoxysilane, vinyl methoxysilane, vinyl tris(β-methoxyethoxy)silane, or the like), a methacrylate-based compound (γ-methacryloxypropyltrimethoxysilane, γ-methacryloxypropylmethyldimethoxysilane, or the like), an epoxy compound (γ-glycidoxypropyltrimethoxysilane, or the like), an isocyanate-based compound (γ-isocyanatopropyltriethoxysilane, or the like), a polymeric silane coupling agent (polymethoxydimethylsiloxane, polyethoxydimethylsiloxane, or the like), and a cationic silane coupling agent (N—(N-benzyl-β-aminoethyl)-γ-aminopropyltrimethoxysilane hydrochloride, or the like).

A thixotrophy imparting agent (thickener) may be blended in the photocurable composition of the invention.

Examples of the thixotrophy imparting agent (thickener) include an inorganic thixotrophy imparting agent (thickener) (bentonite, organically treated bentonite, ultrafinely surface treated calcium carbonate, or the like) and an organic thixotrophy imparting agent (thickener) (hydrogenated castor oil wax, calcium stearate, aluminum oleate, polymerized linseed oil, or the like).

An additive used for a synthetic resin, such as a phenolic antioxidant, a phosphorus-based antioxidant, or a thioether-based antioxidant may be blended in the photocurable composition of the invention to stabilize the composition, if necessary.

Examples of the phenolic antioxidant include 2,6-di-tert-butyl-p-cresol, 2,6-diphenyl-4-octadecyloxy phenol, distearyl (3,5-di-tert-butyl-4-hydroxybenzyl)phosphonate, 1,6-hexamethylenebis[(3,5-di-tert-butyl-4-hydroxyphenyl) propionate amide], 4,4'-thiobis(6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis(4,6-di-tert-butylphenol), 2,2'-ethylidenebis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxy-benzyl)-2,4,6-trimethylbenzene, 2-tert-butyl-4-methyl-6-(2-acryloyloxy-3-tert-butyl-5-methylbenzyl) phenol, stearyl (3,5-di-tert-butyl-4-hydroxyphenyl) propionate, tetrakis[3-(3,5-di-tert-butyl-4-hydroxyphenyl) propionate methyl]methane, thiodiethylene glycol bis[(3,5-di-tert-butyl-4-hydroxyphenyl)propionate], 1,6-hexamethylene bis[(3,5-di-tert-butyl-4-hydroxyphenyl) propionate], bis[3,3-bis(4-hydroxy-3-tert-butylphenyl) butyric acid]glycol ester, bis[2-tert-butyl-4-methyl-6-(2-hydroxy-3-tert-butyl-5-methylbenzyl)phenyl]terephthalate, 1,3,5-[tris(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl)propionyloxy}ethyl]-2,4,8,10-tetraoxaspiro[5,5]undecane, and triethylene glycol bis[(3-tert-butyl-4-hydroxy-5-methylphenyl)propionate].

Examples of the phosphorous-based antioxidant include trisnonylphenyl phosphite, tris[2-tert-butyl-4-(3-tert-butyl- 4-hydroxy-5-methyl-phenylthio)-5-methyl-phenyl]phosphite, tridecyl phosphite, octyl diphenyl phosphite, di(decyl) monophenyl phosphite, di(tridecyl)pentaerythritol diphosphite, di(nonylphenyl)pentaerythritol diphosphite, bis (2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl)isopropylidenediphenol diphosphite, tetra(tridecyl)-4,4'-n-butylidene bis(2-tert-butyl-5-methylphenol)diphosphite, hexa(tridecyl)-1,1,3-tris(2-methyl-4-hydroxy-5-tert-butylphenyl)butane triphosphite, tetrakis(2,4-di-tert-butylphenyl)biphenylene diphosphonite, 9,10-dihydro-9-oxa-10-phosphaphenanthrene-10-oxide, 2,2'-methylenebis (4,6-tert-butylphenyl)-2-ethylhexyl phosphite, 2,2'-methylenebis(4,6-tert-butylphenyl)-octadecyl phosphite, 2,2'-ethylidenebis(4,6-di-tert-butylphenyl)fluoro phosphite, tris(2-[(2,4,8,10-tetrakis-tert-butyldibenzo[d,f][1,3,2]dioxaphosphepin-6-yl)oxy]ethyl)amine, and a phosphite of 2-ethyl-2-butylpropylene glycol and 2,4,6-tri-tert-butylphenol.

Examples of the thioether-based antioxidant include a dialkyl thiodipropionate such as dilauryl thiodipropionate, dimyristyl thiodipropionate, and distearyl thiodipropionate, and a pentaerythritol tetrakis(β alkylthiopropionic acid ester).

A flame retardant used for a synthetic resin, such as a phosphoric acid ester-based flame retardant, a condensed phosphoric acid ester-based flame retardant, or a (poly) phosphoric acid salt-based flame retardant may be blended in the photocurable composition of the invention if necessary.

Examples of the phosphoric acid ester-based flame retardant include trimethyl phosphate, triethyl phosphate, tributyl phosphate, tributoxyethyl phosphate, trischloroethyl phosphate, frisdichloropropyl phosphate, triphenyl phosphate, tricresyl phosphate, cresyl diphenyl phosphate, trixylenyl phosphate, octyl diphenyl phosphate, xylenyl diphenyl phosphate, trisisopropyl phenyl phosphate, 2-ethylhexyl diphenyl phosphate, t-butylphenyl diphenyl phosphate, bis-(t-butylphenyl)phenyl phosphate, tris-(t-butylphenyl)phosphate, isopropylphenyl diphenyl phosphate, bis-(isopropylphenyl)diphenyl phosphate, and tris-(isopropylphenyl) phosphate.

Examples of the condensed phosphoric acid ester-based flame retardant include 1,3-phenylene bis(diphenyl phosphate), 1,3-phenylene bis(dixylenyl phosphate), and bisphenol A bis(diphenyl phosphate).

Examples of the (poly)phosphoric acid salt-based flame retardant include an ammonium salt or amine salt of (poly) phosphoric acid, such as ammonium polyphosphate, melamine polyphosphate, piperazine polyphosphate, melamine pyrophosphate, and piperazine pyrophosphate.

Moreover, a leveling agent (for example, a fluorine-based compound, a silicone-based compound, an acrylic compound, or the like), a colorant (a pigment, a dye, or the like), a cross-linking agent (a polyisocyanate, a melamine, or the like), or a filler (silica, a ceramic powder, a glass powder, a metal powder, alumina, colloidal silica, an inorganic filler, an organic resin filler, or the like) may be blended in the photocurable composition of the invention if necessary.

The photocurable composition of the invention can be diluted by an organic solvent and then used to be coated on a base material. Examples of the organic solvent include an ester-based solvent such as ethyl acetate, propyl acetate, butyl acetate, amyl acetate, benzyl acetate, ethylene glycol monobutyl acetate, butyl lactate, and butyl levulinate, a ketone-based solvent such as methyl ethyl ketone, ethyl butyl ketone, methyl isobutyl ketone, and cyclohexanone, an alcohol-based solvent such as ethylene glycol monomethyl ether, ethylene glycol monoethyl ether, ethylene glycol monobutyl ether, ethylene glycol benzyl ether, ethylene glycol monophenyl ether, propylene glycol monomethyl ether, propylene glycol monoethyl ether, benzyl alcohol, methyl phenyl carbitol, and n-butanol and t-butanol, an aromatic solvent such as benzene, toluene, xylene, and cumene, a halogenated hydrocarbon-based solvent such as methylene dichloride, ethylene dichloride, and chlorobenzene, a petroleum-based solvent such as petroleum ether and petroleum naphtha, and an aliphatic solvent such as n-hexane and cyclohexane. One kind of these may be used singly, or two or more kinds thereof may be concurrently used.

The photocurable composition of the invention is preferably used as a photocurable hard coating agent.

Examples of the base material of the hard coating agent of the invention include a film or sheet of synthetic resin, such as polyester (PET), polypropylene, polyethylene, polyacrylate, polycarbonate, triacetyl cellulose, polyethersulfone, and a cyclo olefin polymer, and a film or sheet of polyester (PET) is particularly preferable. Examples of the base film used in the hard coated film of the invention include the various kinds of film or sheet of synthetic resin exemplified above. These films or sheets may be subjected to various kinds of surface treatment or alignment treatment.

Examples of a method to coat the hard coating agent of the invention on a resin film or sheet of the base material include a bar coater coating, a Meyer bar coating, an air knife coating, a gravure coating, a reverse gravure coating, a micro gravure coating, a micro reverse gravure coater coating, a die coater coating, a dip coating, a spin coat coating, and a spray coating, or a printing method (a gravure printing, a reverse gravure printing, an offset printing, a flexographic printing, and a screen printing).

An ultraviolet irradiation apparatus having a xenon lamp, a high pressure mercury lamp, or a metal halide lamp may be used as a light source in a case in which the photocurable composition or the hard coating agent of the invention is cured by being irradiated with ultraviolet rays. The irradiation amount of ultraviolet rays may be appropriately adjusted.

The photocurable composition of the invention is equipped with characteristics excellent in hardness, scratch resistance, adhesion with the base film, and weather resistance in a case in which the photocurable composition is used as a hard coating agent.

The photocurable composition of the invention is preferably used as a hard coating agent, and the film or sheet of synthetic resin coated with the hard coating agent is excellent in hardness, scratch resistance, transparency, appearance, and weather resistance, and thus is suitably used in an optical film used in a display including a liquid crystal display device, or the like. Specifically, the film or sheet of synthetic resin coated with the hard coating agent can be used in a mobile phone, a smart phone, a personal computer, a PDA (personal digital assistant), and the like, and particularly is suitably used for the touch panel of these.

Examples of other applications of the photocurable composition or the hard coating agent of the invention include a material for personal computer (a pen input personal computer, a touch panel, a display cover, and the like), a household appliance (a television, a radio cassette recorder, a stereo, a case or display of computer game console, and the like), a material for automobiles (a headlight, a glazing, a cover of instrument, and the like), an optical disc, an optical lens (a camera, a video camera, a magnifying glass, and the like), a spectacle lens (for correction, sunglasses, fashion glasses, and the like), sports goods (a ski, a tennis racket, and the like), an organic glass plate, a billboard, a traffic sign, a name plate, a decorative case, a watch lens, a cosmetic container, a housing member, a transfer foil, a transfer film, a dry film resist, and a reflector.

EXAMPLES

Hereinafter, the invention will be further specifically described with reference to Examples and the like, but is not limited to the following Examples and the like.

[Synthetic Example 1] Synthesis of Ultraviolet Absorber (Compound No. 2)

[Chem. 9]

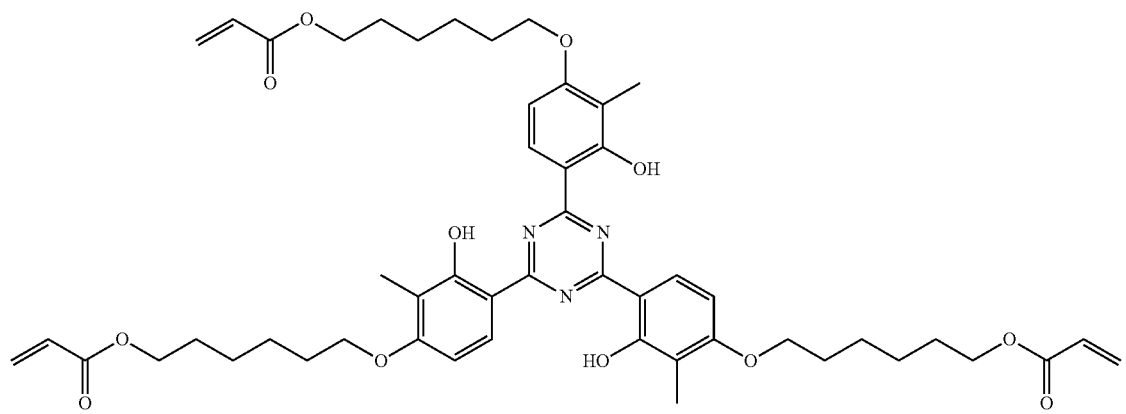

Compound No. 2

First, 2,4,6-tris[2-hydroxy-3-methyl-4-(6-hydroxy)hexyloxyphenyl]triazine (hereinafter, referred to as the intermediate A) is synthesized as an intermediate according to the following procedure.

To a four-necked flask of 300 ml, 10.00 g of 2,4,6-tris(2, 4-dihydroxy-3-methylphenyl)triazine, 5.56 g of calcium carbonate, 50.15 g of cyclohexanone, and 4.18 g of toluene were added and heated to 130° C. Thereto, 10.99 g of 6-chloro-1-hexanol was added dropwise and the resultant was reacted for 9 hours. The neutralization treatment of the reaction product was performed with formic acid, and then the resultant was washed with water and the solvent was removed therefrom under reduced pressure. The residue was recrystallized from cyclohexanone/toluene (3/1), thereby obtaining 12.01 g of pale yellow powder (yield of 72%) having a melting point of 128° C.

Next, 10.00 g of the intermediate A, 0.17 g of p-toluenesulfonic acid monohydrate, and 0.08 g of p-methoxyphenol were added to a four-necked flask of 300 ml, and heated to 105° C. Thereto, 5.78 g of acrylic acid was added dropwise and the resultant was reacted for 12 hours. The reaction product was washed with water, and the solvent was removed therefrom under reduced pressure. The residue was recrystallized from toluene/isopropanol (1/1), thereby obtaining 8.15 g of pale yellow powder (yield of 67%) having a melting point of 91° C. The compound thus obtained was subjected to $^1$H-NMR measurement. The analytical result is presented below. The powder thus obtained was identified as Compound No. 2 by the following analytical result.

$^1$H-NMR (CDCl$_3$) 1.61-1.71 (CH$_2$C$\underline{H}_2$C$\underline{H}_2$CH$_2$), 1.75-1.85 (C$\underline{H}_2$CH$_2$CH$_2$C$\underline{H}_2$), 2.18 (Ar—CH$_3$), 3.99-4.19 (ArOCH$_2$), 4.06-4.26 (C(=O)OCH$_2$), 5.73-5.87 (CH=C$\underline{H}_2$), 5.96-6.25 (C$\underline{H}$=CH$_2$), 6.32-6.53 (CH=C$\underline{H}_2$), 6.51-6.61 (Ar—H), 7.96-8.06 (Ar—H), 13.52 (Ar—OH)

The absorption spectrum of the chloroform solution (concentration of 10 mg/L) of Compound No. 2 thus obtained was measured. The measurement was performed using V-560 manufactured by JASCO Corporation. The absorption spectrum is illustrated in FIG. 1. The maximum absorption wavelength was 356 nm, and the molar extinction coefficient was $\varepsilon=1.41\times10^{-5}$.

[Synthetic Example 2] Synthesis of Ultraviolet Absorber Mixture-1

The ultraviolet absorber mixture-1 represented by the following structural formula was synthesized.

[Chem. 10]

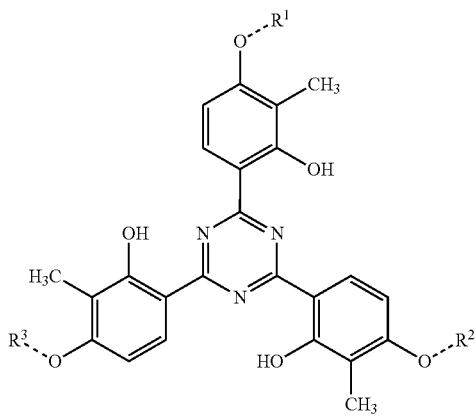

Ultraviolet absorber mixture-1 wherein R¹, R² and R³ represent 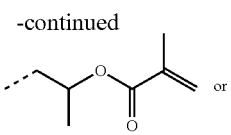 or

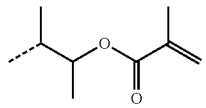

First, an addition product (hereinafter, referred to as the intermediate B) of 2,4,6-tris(2,6-dihydroxy-4-methylphenyl)triazine and propylene carbonate was synthesized as an intermediate according to the following procedure.

To a four-necked flask of 1000 ml, 67.16 g of 2,4,6-tris (2,4-dihydroxy-3-methylphenyl)triazine, 122.59 g of propylene carbonate, 0.80 g of sodium carbonate, and 466.27 g of cyclohexanone were added and heated to 160° C., and then reacted for 16 hours. The neutralization treatment of the reaction product was performed with formic acid, and then the solvent was removed therefrom under reduced pressure. The residue was recrystallized from dimethylformamide/isopropanol (1/3), thereby obtaining 74.22 g of pale yellow powder (yield of 80%) having a melting point of 136° C.

Next, 1.50 g of the intermediate B, 0.55 g of p-toluenesulfonic acid monohydrate, and 0.09 g of p-methoxyphenol were added to a four-necked flask of 50 ml, and heated to 105° C. Thereto, 6.23 g of methacrylic acid was added dropwise and the resultant was reacted for 10 hours. The reaction product was washed with water and the solvent was removed therefrom under reduced pressure, thereby obtaining 0.81 g of pale yellow powder (yield of 41%) having a melting point of 118° C. The compound thus obtained was subjected to $^1$H-NMR measurement. The analytical result is presented below. The powder thus obtained was identified as the ultraviolet absorber mixture-1 by the following analytical result.

$^1$H-NMR (CDCl$_3$) 1.42-1.49 (OCHC$\underline{H}_3$), 1.96 (CH$_2$=CC$\underline{H}_3$), 2.15 (Ar—CH$_3$), 4.10-4.16 (OCH$_2$), 5.29-5.48 (OC$\underline{H}$CH$_3$), 5.56-5.60 (C$\underline{H}_2$=CCH$_3$), 6.11-6.13 (C$\underline{H}_2$=CCH$_3$), 6.50-6.60 (Ar—H), 7.93-8.03 (Ar—H), 13.45 (Ar—OH)

Figure 2:
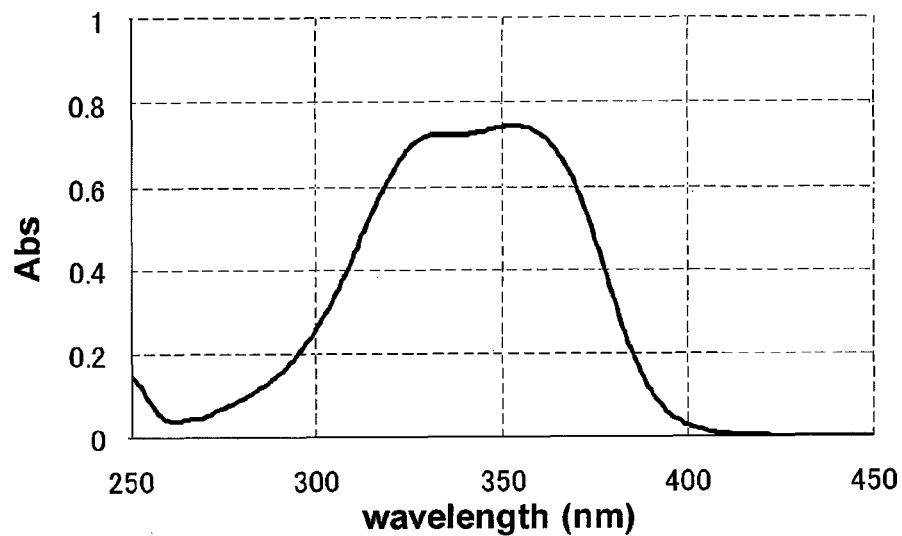
FIG. 2 is an absorption spectrum of the ultraviolet absorber mixture-1 obtained in Synthesis Example 2.

The absorption spectrum of the chloroform solution (concentration of 10 mg/L) of the ultraviolet absorber mixture-1 thus obtained was measured. The measurement was performed using V-560 manufactured by JASCO Corporation. The absorption spectrum is illustrated in FIG. 2. The maximum absorption wavelength was 354 nm, and the molar extinction coefficient was ε=1.34×10$^{-5}$.

[Examples 1 and 2 and Comparative Examples 1 to 3] Production and Evaluation of Photocurable Composition (Hard Coating Agent)

In Examples 1 and 2, a hard coating agent of photocurable composition was obtained using the ultraviolet absorber of Compound No. 2 obtained in the synthetic example 1 or the ultraviolet absorber mixture-1 obtained in Synthetic Example 2 in the proportion described in Table 1. The hard coating agent thus obtained was coated on an interference fringe measure treated PET (O321 manufactured by Mitsubishi Plastic, Inc.) using a bar coater such that the film thickness after drying and curing becomes 5 μm or 10 μm, thereby forming a film layer. The film layer was dried at 80° C. for 1 minute, and then irradiated with ultraviolet rays of 300 mJ/cm² using an ultraviolet irradiation apparatus (F300S manufactured by Heraeus Noblelight Fusion UV Inc.) under a nitrogen atmosphere.

Performance evaluation with regard to the hard coated film thus obtained was performed by the following method. The evaluation result is listed in Table 1.

In Comparative Example 1, a hard coated film was obtained in the same manner as Example 1 except that an ultraviolet absorber was not used, and the hard coated film thus obtained was subjected to the performance evaluation. In Comparative Examples 2 and 3, a hard coated film was obtained in the same manner as Example 1 except that Tinuvin 477 (manufactured by BASF) of a commercially available triazine-based ultraviolet absorber is used in the proportional amount described in Table 1 instead of Compound No. 2, and the hard coated film thus obtained was subjected to the performance evaluation. The evaluation result is listed in Table 1.

[Examples 3 and 4 and Comparative Examples 4 to 6] Production and Evaluation of Photocurable Composition (Hard Coating Agent)

In Examples 3 and 4, a hard coated film was obtained in the same manner as Example 1 except that the film base material was changed from the interference fringe measure treated PET to an easy adhesion treated PET (A-4300 manufactured by TOYOBO CO., LTD.), and the hard coated film thus obtained was subjected to the performance evaluation. The evaluation result is listed in Table 2. In Comparative Example 4, a hard coated film was obtained in the same manner as Example 3 except that an ultraviolet absorber was not used, and the hard coated film thus obtained was subjected to the performance evaluation. In Comparative Examples 5 and 6, a hard coated film was obtained in the same manner as Example 3 except that Tinuvin 477 (manufactured by BASF) of a commercially available triazine-based ultraviolet absorber is used in the proportional amount described in Table 2 instead of Compound No. 2, and the hard coated film thus obtained was subjected to the performance evaluation. The evaluation result is listed in Table 2.

Examples 5 and 6 and Comparative Examples 7 to 9

In Examples 5 and 6, a hard coated film was obtained in the same manner as Example 3 except that the irradiation with ultraviolet rays was performed under the atmosphere instead of under the nitrogen atmosphere, and the hard coated film thus obtained was subjected to the performance evaluation. The evaluation result is listed in Table 3. In Comparative Example 7, a hard coated film was obtained in the same manner as Example 5 except that an ultraviolet absorber was not used, and the hard coated film thus obtained was subjected to the performance evaluation. In Comparative Examples 8 and 9, a hard coated film was obtained in the same manner as Example 5 except that Tinuvin 477 (manufactured by BASF) of a commercially available triazine-based ultraviolet absorber is used in the proportional amount described in Table 3 instead of Compound No. 2, and the hard coated film thus obtained was subjected to the performance evaluation. The evaluation result is listed in Table 3.

<Performance Evaluation Method>

(1) Haze (Opacity)

The haze value (%) of the hard coated film was measured based on JIS K7105 and JIS K7136.

(2) Total Light Transmittance (Transparency)

The total light transmittance (%) with respect to the hard coated film was measured based on JIS K7105 and JIS K7136.

(3) UV Transmittance

The transmittance (%) of ultraviolet rays at 365 nm and 380 nm with respect to the hard coated film was measured. The measurement was performed using V-670 manufactured by JASCO Corporation.

(4) Pencil Hardness

The pencil hardness was measured based on JIS K5600-5-4 in a state that a pencil was at an angle of 45 degrees with respect to the coated surface of the hard coated film and under a load of 750 g.

(5) Adhesion Test

With regard to the hard coated film, scratches were formed on the surface of the hard coating layer at 1 mm intervals using a cutter, and thus 100 squares were prepared. The cellophane tape was pasted thereon and then was peeled off therefrom at an angle of 60 degrees. Thereafter, the number of squares, in which the coated film was not peeled off but remains, among the 100 squares were counted. The adhesion was evaluated by the number.

(6) Scratch Resistance Test

The steel wool No. 0000 was traveled back and forth 20 times on the hard coated film under a load of 2 kg per 1 cm² using a load variation type friction and wear measurement system (TRIBOGEAR HHS2000 manufactured by SHINTO Scientific Co., ltd.), and then the state of scratches was visually observed as it was (under natural light) and under a green light, thereby performing the evaluation according to the following criteria.

The highest in evaluation is 5 points and the lowest in evaluation is 0 point.

Points: there are no scratches at all.
4 Points: 1 to 5 scratches are acknowledged.
3 Points: 6 to 15 scratches are acknowledged.
2 Points: 16 to 30 scratches are acknowledged.
1 Point: a large number of scratches are acknowledged.
0 Point: scratches are acknowledged on the entire surface.

(7) Curling Property

The hard coated film was cut to 10 cm×10 cm. First, the left half (corresponding to 5 cm) was weighted with a glass plate and the height of each of the two corners at the right side that was warped up was measured. Next, the right half (corresponding to 5 cm) was weighted with a glass plate and the height of each of the two corners at the left side that was warped up was measured. The average value (unit: mm) of the four measured values was regarded as the curling property.

TABLE 1

|  | Examples | | | | Comparative Examples | | | | | |
| --- | --- | --- | --- | --- | --- | --- | --- | --- | --- | --- |
|  | 1-1 | 1-2 | 2-1 | 2-2 | 1-1 | 1-2 | 2-1 | 2-2 | 3-1 | 3-2 |
| Compound No. 2 | 5.0 | 5.0 |  |  |  |  |  |  |  |  |
| Ultraviolet absorber mixture-1 |  |  | 5.0 | 5.0 |  |  |  |  |  |  |
| TINUVIN477 |  |  |  |  |  |  | 5.0 | 5.0 | 7.5 | 7.5 |
| Ultraviolet curable resin-1*[1] | 10 | 10 | 10 | 10 | 10 | 10 | 10 | 10 | 10 | 10 |
| Ultraviolet curable resin-2*[2] | 90 | 90 | 90 | 90 | 90 | 90 | 90 | 90 | 90 | 90 |
| Photopolymerization initiator-1*[3] | 0.2 | 0.2 | 0.2 | 0.2 | 0.2 | 0.2 | 0.2 | 0.2 | 0.2 | 0.2 |
| Photopolymerization initiator-2*[4] | 11 | 11 | 11 | 11 | 11 | 11 | 11 | 11 | 11 | 11 |
| Leveling agent*[5] | 0.1 | 0.1 | 0.1 | 0.1 | 0.1 | 0.1 | 0.1 | 0.1 | 0.1 | 0.1 |
| Propylene glycol monomethyl ether | 70 | 70 | 70 | 70 | 70 | 70 | 70 | 70 | 70 | 70 |
| Methyl ethyl ketone | 45 | 45 | 45 | 45 | 45 | 45 | 45 | 45 | 45 | 45 |
| Film thickness (μm) | 5 | 10 | 5 | 10 | 5 | 10 | 5 | 10 | 5 | 10 |
| Haze (%) | 1.1 | 1.02 | 1.1 | 1.01 | 1.04 | 0.96 | 1.06 | 0.99 | 1.08 | 1.02 |
| Total light transmittance (%) | 91.2 | 91.8 | 90.9 | 91.1 | 91.0 | 91.0 | 90.9 | 91.2 | 91.0 | 91.6 |
| Transmittance/380 nm (%) | 18.5 | 7.01 | 19.7 | 7.6 | 99.2 | 95.8 | 37.4 | 15.1 | 23.4 | 6.0 |
| Transmittance/365 nm (%) | 5.38 | 0.98 | 6.2 | 1.2 | 98.1 | 92.8 | 14.2 | 2.11 | 5.2 | 0.3 |
| Pencil hardness | 3H | 3H | 2H | 2H | 2H | 2H | 2H | 2H | 2H | 2H |
| Adhesion test | 100 | 100 | 100 | 100 | 100 | 100 | 80 | 85 | 80 | 85 |
| Scratch resistance test Natural light/green light | 5/4 | 5/4 | 5/4 | 5/4 | 5/5 | 5/5 | 4/3 | 4/3 | 4/3 | 4/3 |
| Curling property (mm) | 7.1 | 26.8 | 7.3 | 27.5 | 7.3 | 26.3 | 10.2 | 27.0 | 10.6 | 27.3 |

*[1]Mixture of polyurethane acrylate and 1-hydroxycyclohexyl phenyl ketone, Product Name: BEAM SET 575CB manufacture by Arakawa Chemical Industries, Ltd.
*[2]Acrylic resin, Product Name: EM265 manufacture by ETERNAL CHEMICAL CO., LTD.
*[3]Diphenyl-(2,4,6-trimethylbenzoyl)phosphine oxide, Product Name: SP-246 manufacture by ADEKA CORPORATION
*[4]1-hydroxycyclohexyl phenyl ketone, Product Name: Esacure KS300 manufacture by DKSH management Ltd./DKSH Holding Ltd.
*[5]Product Name: BYK-375 manufacture by BYK Japan

TABLE 2

|  | Examples | | Comparative Examples | | |
| --- | --- | --- | --- | --- | --- |
|  | 3-1 | 4-1 | 4-1 | 5-1 | 6-1 |
| Compound No. 2 | 5.0 |  |  |  |  |
| Ultraviolet absorber mixture-1 |  | 5.0 |  |  |  |
| TINUVIN477 |  |  |  | 5.0 | 7.5 |
| Ultraviolet curable resin-1*[1] | 10 | 10 | 10 | 10 | 10 |
| Ultraviolet curable resin-2*[2] | 90 | 90 | 90 | 90 | 90 |
| Photopolymerization initiator-1*[3] | 0.2 | 0.2 | 0.2 | 0.2 | 0.2 |
| Photopolymerization initiator-2*[4] | 11 | 11 | 11 | 11 | 11 |
| Leveling agent*[5] | 0.1 | 0.1 | 0.1 | 0.1 | 0.1 |
| Propylene glycol monomethyl ether | 70 | 70 | 70 | 70 | 70 |
| Methyl ethyl ketone | 45 | 45 | 45 | 45 | 45 |
| Film thickness (μm) | 5 | 5 | 5 | 5 | 5 |
| Haze(%) | 0.91 | 0.72 | 0.72 | 0.96 | 1.01 |
| Total light transmittance (%) | 91.6 | 91.4 | 91.6 | 91.7 | 91.4 |
| Transmittance/380 nm (%) | 19.3 | 20.6 | 99.8 | 39.4 | 24.6 |
| Transmittance/365 nm (%) | 5.9 | 6.8 | 99.0 | 15.5 | 5.7 |
| Pencil hardness | 3H | 3H | 2H | H | H |

TABLE 2-continued

|  | Examples | | Comparative Examples | | |
|---|---|---|---|---|---|
|  | 3-1 | 4-1 | 4-1 | 5-1 | 6-1 |
| Adhesion test | 100 | 100 | 100 | 90 | 90 |
| Scratch resistance test | 5/4 | 5/4 | 5/4 | 5/4 | 5/4 |
| Natural light/green light |  |  |  |  |  |
| Curling property (mm) | 7.2 | 7.3 | 6.3 | 7.2 | 7.3 |

*[1] Mixture of polyurethane acrylate and 1-hydroxycyclohexyl phenyl ketone, Product Name: BEAM SET 575CB manufacture by Arakawa Chemical Industries, Ltd.
*[2] Acrylic resin, Product Name: EM265 manufacture by ETERNAL CHEMICAL CO., LTD.
*[3] Diphenyl-(2,4,6-trimethylbenzoyl)phosphine oxide, Product Name: SP-246 manufacture by ADEKA CORPORATION
*[4] 1-hydroxycyclohexyl phenyl ketone, Product Name: Esacure KS300 manufacture by DKSH management Ltd/DKSH Holding Ltd.
*[5] Product Name: BYK-375 manufacture by BYK Japan

TABLE 3

|  | Examples | | Comparative Examples | | |
|---|---|---|---|---|---|
|  | 5-1 | 6-1 | 7-1 | 8-1 | 9-1 |
| Compound No. 2 | 5.0 |  |  |  |  |
| Ultraviolet absorber mixture-1 |  | 5.0 |  |  |  |
| TINUVIN477 |  |  |  | 5.0 | 7.5 |
| Ultraviolet curable resin-1*[1] | 10 | 10 | 10 | 10 | 10 |
| Ultraviolet curable resin-2*[2] | 90 | 90 | 90 | 90 | 90 |
| Photopolymerization initiator-1*[3] | 0.2 | 0.2 | 0.2 | 0.2 | 0.2 |
| Photopolymerization initiator-2*[4] | 11 | 11 | 11 | 11 | 11 |
| Leveling agent*[5] | 0.1 | 0.1 | 0.1 | 0.1 | 0.1 |
| Propylene glycol monomethyl ether | 70 | 70 | 70 | 70 | 70 |
| Methyl ethyl ketone | 45 | 45 | 45 | 45 | 45 |
| Film thickness (μm) | 5 | 5 | 5 | 5 | 5 |
| Haze(%) | 0.66 | 0.67 | 0.82 | 0.91 | 1.10 |
| Total light transmittance (%) | 91.2 | 91.5 | 91.3 | 91.5 | 91.7 |
| Transmittance/380 nm (%) | 19.2 | 19.9 | 99.9 | 36.9 | 22.4 |
| Transmittance/365 nm (%) | 6.8 | 6.3 | 97.1 | 16.2 | 6.1 |
| Pencil hardness | 2H | 2H | 2H | H | H |
| Adhesion test | 100 | 100 | 100 | 85 | 85 |
| Scratch resistance test | 5/4 | 5/4 | 5/5 | 4/3 | 4/3 |
| Natural light/green light |  |  |  |  |  |
| Curling property (mm) | 9.5 | 9.5 | 9.5 | 9.6 | 9.4 |

*[1] Mixture of polyurethane acrylate and 1-hydroxycyclohexyl phenyl ketone, Product Name: BEAM SET 575CB manufacture by Arakawa Chemical Industries, Ltd.
*[2] Acrylic resin, Product Name: EM265 manufacture by ETERNAL CHEMICAL CO., LTD.
*[3] Diphenyl-(2,4,6-trimethylbenzoyl)phosphine oxide, Product Name: SP-246 manufacture by ADEKA CORPORATION
*[4] 1-hydroxycyclohexyl phenyl ketone, Product Name: Esacure KS300 manufacture by DKSH management Ltd/DKSH Holding Ltd.
*[5] Product Name: BYK-375 manufacture by BYK Japan

The invention claimed is:

1. A photocurable composition comprising:
   one or more kinds of ultraviolet absorbers represented by the following Formula (1):

[Chem. 1]

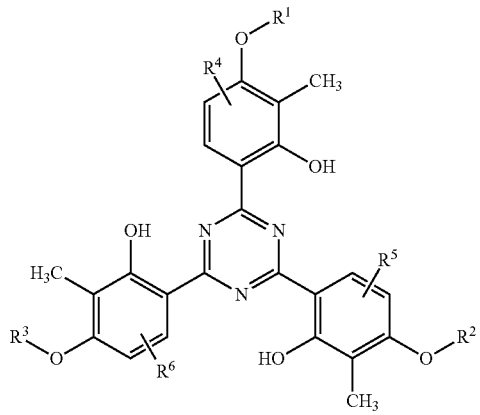

(1)

wherein $R^1$, $R^2$ and $R^3$ may be the same as or different from each other and represent a branched or linear alkyl group that has from 3 to 8 carbon atoms and is substituted with a (meth)acryloyloxy group; the alkyl group may be substituted with a hydroxyl group, the alkyl group may be interrupted by one or more selected from an oxygen atom, a carbonyl group, an ester group, and an amide group; and $R^4$, $R^5$ and $R^6$ may be the same as or different from each other and represent a hydrogen atom, or an alkyl group having from 1 to 12 carbon atoms; and
   one or more kinds selected from the group consisting of photocurable monomer, photocurable oligomer, and photocurable polymer, and one or more kinds of photopolymerization initiator, the photopolymerization initiator being one or more kinds selected from the group consisting of (1) benzophenone or its derivatives, (2) acetophenone derivatives, (3) thioxanthone or its derivatives, (4) benzyl or its derivatives, (5) benzoin or its derivatives, (6) oxime-based compounds, (7) α-hydroxy ketone-based compounds, (8) α-aminoalkylphenone-based compounds, (9) phosphine oxide-based compounds and (10) titanocene compounds, wherein the photocurable composition forms a film having a transmission at 380 nm of 7.01% to 20.6%, and a transmission at 365 nm of from 0.98% to 6.8%.

2. The photocurable composition according to claim 1, wherein the photocurable monomer, the photocurable oligomer, and the photocurable polymer have at least one (meth)acryloyl group.

3. A hard coating agent comprising the photocurable composition according to claim 1.

4. A hard coated film comprising a hard coating layer formed on a base film using the hard coating agent according to claim 3.

5. A hard coating agent comprising the photocurable composition according to claim 2.

6. A hard coated film comprising a hard coating layer formed on a base film using the hard coating agent according to claim 5.

7. The photocurable composition according to claim 1, wherein $R^1$, $R^2$ and $R^3$ may be the same as or different from each other and represent a branched or linear alkyl group selected from the group consisting of n-propyl, isopropyl, n-butyl, isobutyl, sec-butyl, tert-butyl, n-pentyl, isopentyl, neopentyl, tert-amyl, 1,2-dimethylpropyl, n-hexyl, cyclohexyl, 1,3-dimethylbutyl, 1-isopropylpropyl, 1,2-dimethylbutyl, n-heptyl, 2-heptyl, 1,4-dimethylpentyl, tert-heptyl, 2-methyl-1-isopropylpropyl, 1-ethyl-3-methylbutyl, n-octyl, tert-octyl, 2-ethylhexyl, and 2-methylhexyl.

8. A hard coating agent comprising the photocurable composition according to claim 7.

9. A hard coated film comprising a hard coating layer formed on a base film using the hard coating agent according to claim 8.

10. The photocurable composition according to claim 1, wherein $R^1$, $R^2$ and $R^3$ may be the same as or different from each other and represent a branched or linear alkyl group that has from 3 to 6 carbon atoms and is substituted with a (meth)acryloyloxy group.

11. The photocurable composition according to claim 1, wherein the photopolymerization initiator is present at 0.1 to 10% by mass in the solid components of the photocurable composition.

12. A photocurable composition comprising:
one or more kinds of ultraviolet absorbers represented by the following Formula (1):

[Chem. 1]

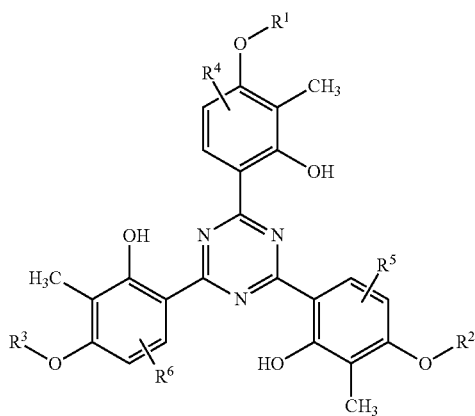

(1)

wherein $R^1$, $R^2$ and $R^3$ may be the same as or different from each other and represent a branched or linear alkyl group that has from 3 to 20 carbon atoms and is substituted with a (meth)acryloyloxy group; the alkyl group may be substituted with a hydroxyl group, the alkyl group may be interrupted by one or more selected from an oxygen atom, a carbonyl group, an ester group, and an amide group; and $R^4$, $R^5$ and $R^6$ may be the same as or different from each other and represent a hydrogen atom, or an alkyl group having from 1 to 12 carbon atoms; and one or more kinds selected from the group consisting of photocurable monomer, photocurable oligomer, and photocurable polymer, and one or more kinds of photopolymerization initiator, the photopolymerization initiator being one or more kinds selected from the group consisting of (1) benzophenone or its derivatives, (2) acetophenone derivatives, (3) thioxanthone or its derivatives, (4) benzyl or its derivatives, (5) benzoin or its derivatives, (6) oxime-based compounds, (7) α-hydroxy ketone-based compounds, (8) α-aminoalkylphenone-based compounds, (9) phosphine oxide-based compounds and (10) titanocene compounds, wherein
the photocurable composition forms a film having a transmission at 380 nm of 7.01% to 20.6%, and a transmission at 365 nm of from 0.98% to 6.8%.

13. The photocurable composition according to claim 12, wherein the photocurable monomer, the photocurable oligomer, and the photocurable polymer have at least one (meth)acryloyl group.

14. A hard coating agent comprising the photocurable composition according to claim 12.

15. The photocurable composition according to claim 12, wherein $R^1$, $R^2$ and $R^3$ may be the same as or different from each other and represent a branched or linear alkyl group selected from the group consisting of n-propyl, isopropyl, n-butyl, isobutyl, sec-butyl, tert-butyl, n-pentyl, isopentyl, neopentyl, tert-amyl, 1,2-dimethylpropyl, n-hexyl, cyclohexyl, 1,3-dimethylbutyl, 1-isopropylpropyl, 1,2-dimethylbutyl, n-heptyl, 2-heptyl, 1,4-dimethylpentyl, tert-heptyl, 2-methyl-1-isopropylpropyl, 1-ethyl-3-methylbutyl, n-octyl, tert-octyl, 2-ethylhexyl, and 2-methylhexyl, 2-propylhexyl, 10 n-nonyl, isononyl, n-decyl, isodecyl, n-undecyl, isoundecyl, n-dodecyl, isododecyl, n-tridecyl, isotridecyl, n-tetradecyl, isotetradecyl, n-pentadecyl, isopentadecyl, n-hexadecyl, isohexadecyl, n-heptadecyl, isoheptadecyl, n-octadecyl, isooctadecyl, n-nonadecyl, isononadecyl, n-icosyl, and isoicosyl, and is substituted with a (meth)acryloyloxy group.

16. The photocurable composition according to claim 12, wherein the photopolymerization initiator is present at 0.1 to 10% by mass in the solid components of the photocurable composition.

* * * * *